United States Patent [19]

Sakata et al.

[11] Patent Number: 5,225,343
[45] Date of Patent: Jul. 6, 1993

[54] PROCESS FOR PREPARATION OF AN ADVENTIVE EMBRYO OF PODOPHYLLUM

[75] Inventors: Ko Sakata; Eitaroh Morita; Tetsuya Takezono, all of Yokohama, Japan

[73] Assignee: Nippon Oil Company, Ltd., Tokyo, Japan

[21] Appl. No.: 603,361

[22] Filed: Oct. 26, 1990

[30] Foreign Application Priority Data

Oct. 26, 1989 [JP] Japan .................................. 1-277223
Mar. 14, 1990 [JP] Japan .................................. 2-61098
Mar. 14, 1990 [JP] Japan .................................. 2-61099

[51] Int. Cl.$^5$ .......................... C12N 5/00; C12N 5/02
[52] U.S. Cl. .......................... 435/240.45; 435/240.46; 435/240.48; 435/240.49
[58] Field of Search ........... 435/240.4, 240.45, 240.48, 435/240.49, 240.46

[56] References Cited

U.S. PATENT DOCUMENTS 4,038,778  8/1977  Kadkade .............................. 435/243

FOREIGN PATENT DOCUMENTS 0169486  9/1984  Japan .............................. 435/240.48

OTHER PUBLICATIONS

Arumugan et al., Can. J. Bot., 68(3), 1990, pp. 487-491 (Biosis Abstract #90000042).

Primary Examiner—Douglas W. Robinson
Assistant Examiner—Susan M. Weber
Attorney, Agent, or Firm—Wegner, Cantor, Mueller & Player

[57] ABSTRACT

A process for the preparation of an adventive embryo of a plant belonging to the genus Podophyllum, comprising the steps of preparing cells of a plant belonging to the genus Podophyllum, incubating the cells in a sugar free medium or a medium containing up to 2% by weight sugar, and then incubating the cells in a medium containing more than 2% by weight of sugar to generate an adventive embryo; a process for the production of a podophyllotoxin compound comprising the steps of preparing an adventive embryo of a plant belonging to the genus Podophyllum, culturing the adventive embryo to generate an adventitious organ, culturing the adventitious organ to produce a podophyllotoxin compound, and recovering the podophyllotoxin compound; and a process for the production of a podophyllotoxin compound, comprising the steps of preparing de-differentiated cells or tissue of a plant belonging to the genus Podophyllum culturing the de-differentiated cells or tissue in a liquid medium to generate a differentiated organ, culturing the differentiated organ on a solid medium to produce a podophyllotoxin compound, and recovering the podophyllotoxin compound.

1 Claim, No Drawings

PROCESS FOR PREPARATION OF AN ADVENTIVE EMBRYO OF PODOPHYLLUM

BACKGROUND OF THE INVENTION

1. Field of the Invention

The present invention relates to processes for the production of podophyllotoxin compounds by culturing Podophyllum, and to the preparation of an adventive embryo useful for such processes.

2. Description of the Related Art

Perennial plants belonging to the genus Podophyllum are important foliage plants, and recently have been found to produce podophyllotoxin compounds and flavonoid compounds which are useful in the fields of pharmaceuticals and cosmetics, and therefore, have become industrially valuable. For example, podophyllotoxin, one of the podophyllotoxin compounds, was found to have an aperitive activity and antimicrobial activity, and has been used as an aperitive medicament or antimicrobial agent. Moreover, recently, podophyllotoxin has atracted attention as an anti-tumor agent, and the development of anti-tumor agents derived from podophyllotoxin compounds is underway.

Nevertheless, in the industrial production of the podophyllotoxin compounds many problems arise, as in the industrial production of other substances of a higher plant origin. Namely, although to produce such substances it is necessary to obtain a naturally occurring desired plant and to cultivate the plant, the production of the desired product by cultivating the plant is accompanied by various limitations. For example, the productivity of a desired product varies according to various conditions, including environmental conditions, and in general the productivity is relatively low. Therefore, it is very difficult to consistently obtain a large amount of Podophyllum plant as an industrial starting material for the production of podophyllotoxin compounds.

To resolve the above-mentioned problems accompanying the use of the plant, the use of a plant tissue culture has been proposed. In the tissue culture method, cells or tissue such as callus, dedifferentiated cells, adventive embryo, adventitious organ, or the like are cultured in a medium to accumulate a desired product in the culture medium, which product is then recovered.

General procedures for generating and culturing the above-mentioned plant entities are known, but particular conditions for the generation and culturing of the plant entities differ depending on the plant, and conditions suitable for one particular plant are not necessarily suitable for another plant. Further, the conditions for the production of a particular substance are very strict, and conditions suitable for a particular producer plant, or for a particular product, cannot be automatically applied to the production of an other product or an other plant. Therefore, the conditions for the production must be experimentally determined for each particular plant and each particular product.

Japanese Unexamined Patent Publication No. 62-96088 describes a process for obtaining podophyllotoxin compounds in an amount of 0.0035% by weight relative to the plant mass by culturing an explant of a Podophyllum plant on a solid medium to form a callus, which is then cultured on a solid medium to form a large amount of callus/adventitious roots, and extracting podophyllotoxin compounds from the roots. According to this method, however, the preparation of a large amount of adventitious roots is not always easy, and an accumulated amount of podophyllotoxin compounds is not always satisfactory.

An adventive embryo is useful as a starting or intermediate material for a plant tissue culture for the production of a desired substance, although it is also industrially useful as a starting or intermediate material for the mass-proliferation of plants, in the interests of an efficient breeding and efficient cultivation of the plants, and as a main component of artificial seeds.

Nevertheless, it is very difficult to reproducibly generate an adventive embryo, and to date, the generation of an adventive embryo has been reported only for a very limited plant species. Moreover, in most cases, since the generation of an adventive embryo is carried out on a solid medium, the generation of the adventive embryo takes a relatively long time and the recovery of the adventive embryo is difficult, resulting in an impracticality for an industrial application.

To obtain an adventive embryo as a starting material of the proliferation and tissue culture of useful plants, various methods have been proposed. According to one method, non-differentiated cells of a desired plant are cultured in the presence of plant growth hormones such as auxin to induce the generation of an adventive embryo. According to another method, an osmotic pressure of a medium for culturing a non-differentiated cell is changed to induce the generation of an adventive embryo without using plant growth modulators. These methods however, can not be universally applied to all plants, since the conditions for the generation of an adventive embryo differ depending on particular plants. Further, the generation of an adventive embryo of plants belonging to the genus Podophyllum is not known.

SUMMARY OF THE INVENTION

Accordingly, the present invention provides a process for the preparation of an adventive embryo of a plant belonging to the genus Podophyllum, comprising the steps of:

preparing cells of a plant belonging to the genus Podophyllum;

incubating the cells in a sugar free medium or a medium containing up to 2% by weight sugar; and then incubating the cells in a medium containing more than 2% by weight sugar to generate an adventive embryo.

Moreover, the present invention provides a process for the production of a podophyllotoxin compound comprising the steps of:

preparing an adventive embryo of a plant belonging to the genus Podophyllum;

culturing the adventive embryo to generate an adventitious organ;

culturing the adventitious organ to produce a podophyllotoxin compound; and recovering the podophyllotoxin compound.

The present invention still further provides a process for the production of a podophyllotoxin compound, comprising the steps of:

preparing de-differentiated cells or a tissue of a plant belonging to the genus Podophyllum;

culturing the de-differentiated cells or tissue in a liquid medium to generate a differentiated organ;

culturing the differentiated organ on a solid medium to produce a podophyllotoxin compound; and recovering the podophyllotoxin compound.

DESCRIPTION OF THE PREFERRED EMBODIMENTS

According to the present inventions, any plants belonging to the genus Podophyllum, such as *Podophyllum peltatum, P. emodi, P. hexandrum, P. pleianthum, P. versipelle*, etc., can be used.

Preparation of Cells of Podophyllum Plant

The present processes involve a step for preparing Podophyllum plant cells; the cells are usually in the form of a callus or cells in a liquid culture.

The callus can be obtained according to a conventional procedure. For example, a leaf, stem, root or the like of Podophyllum plant is washed with water, sterilized with an ethanol aqueous solution, a sodium hypochlorite aqueous solution, a benzalconium chloride aqueous solution or the like, and rinsed with sterile water. Then, if necessary or preferable, the plant part is cut into sections, and the sterilized plant parts or sections thus prepared are put on a medium in a flask or petri dish, which is then incubated. Any medium generally used for a plant tissue culture can be used. Prepared examples of such media are Murashige-Skoog medium, Gamborg B5 medium, Nitsch & Nitsch medium, White's medium and the like, supplemented with vitamins and plant growth modulators. The plant growth modulators include auxins such as indole-3-acetic acid, α-naphthalene acetic acid, 2,4-dichlorophenoxyacetic acid and the like; and cytokinins such as kinetin, 6-benzyladenine and the like, and are used alone or in combination. After the plant parts or sections are cultured on the above-mentioned medium at 20° C. to 30° C. for 1 to 4 weeks, a callus of Podophyllum plant is formed.

Culturing of the callus on either a solid medium or in a liquid medium provides liquid culture cells.

In the present invention, "culturing" includes culturing of Podophyllum plant on a solid medium or in a liquid medium. The solid culturing is carried out by putting the cells described above on an aqueous gel containing the above-mentioned medium components. The aqueous gel is preferably agar gel, gellan gum gel or the like. The liquid culture is a culture wherein at least a part of cells to be cultured are in contact with a liquid medium during the culturing, and includes, for example, culturing in an aeration/agitation fermenter, an air-lift fermenter, or in a conical flask on a reciprocating or rotating shaker, and culturing by a paper wick method.

Generation of Adventive Embryo

According to the present invention, an adventive embryo is generated by culturing cells such as a callus, or liquid culture cells of Podophyllum plant are shortly subjected to a starvation condition to a short enough extent that the plant cells survive. Generally, to maintain and grow a culture of Podophyllum plant in a living state for a long time, the presence of a sugar at a concentration of more than 2% by weight is preferable. To subject the culture to the starvation condition, the culture is incubated in a medium containing up to 2% by weight, preferably up to 1.5% by weight, more preferably up to 1.0% by weight, for example, 0.5% by weight, of sugar. Although a sugar-free medium can be used in the starvation step, since an incubation for a long time, for example, for longer than 10 weeks, may result in the death of the culture, an incubation in a sugar-free medium for a long time is not preferable.

The starvation medium is, for example, Murashige-Skoog medium, Gamborg B5 medium, Nitsch & Nitsch medium or the modification thereof optionally supplemented with additional nutrient source and/or plant growth modulators. The nutrient source is, for example, casein hydrolyzate and coconut milk. The plant growth modulators are auxins and cytokinins, which are used alone or in combination, at a concentration of up to 3 mM. The incubation is carried out usually for 2 days to 10 weeks, depending on the sugar concentration of the starvation medium and other factors.

Following the starvation step, the starved plant culture is cultured in a medium having a normal sugar concentration of, for example, more than 2% by weight, more preferably at least 2.5% by weight, for example, 3% by weight.

The above-mentioned medium having a normal sugar concentration is, for example, Murashige-Skoog medium, Gamborg's B5 medium, Nitsch & Nitsch medium or a modification thereof supplemented with sugar, as well as optionally with magnesium ions, a nutrient source and/or plant growth modulators. The magnesium ions accelerate the generation of adventive embryo. As the nutrient source, casein hydrolyzate and coconut milk may be used. The plant growth modulators are auxins and cytokinins, which are used alone or in combination at a concentration of up to 3 mM. The culturing is usually carried out for 2 days to 5 weeks, to generate an adventive embryo in the culture product.

Throughout the above-mentioned starvation under a sugar deficiency and culturing in a normal sugar concentration, the culturing temperature is about 10° C. to 30° C.; the sugar is, for example, sucrose, glucose or galactose; and the culturing is carried out under either light or dark conditions.

According to the present process, an industrially valuable adventive embryo of Podophyllum plants can be easily produced without the hindrances of a low availability of plants and the natural environment.

The adventive embryo in the culture medium thus obtained can be used as a starting material for the generation of an adventitious organ, or the adventive embryo can be isolated, for example, by tweezers in the case of a solid culture or by filtration in the case of a liquid culture, and the isolated adventive embryo can be used to generate an adventitious organ, or in other ways.

Generation of Adventitious Organ

In the present invention, the term "adventitious organ" means tissues having a morphology of an adventitious root or adventitious shoot among the tissues derived from an adventive embryo by culturing the latter in a liquid medium or on a solid medium.

The adventitious organ can be generated by culturing an adventive embryo of the Podophyllum plant in a suitable medium under suitable culture conditions. The culturing can be carried out on a solid medium or in a liquid medium. The medium is preferably Murashige-Skoog medium, Linsmaier-Skoog medium, Nitsch & Nitsch medium or Gamboeg B5 medium supplemented with vitamins.

The medium preferably contains plant growth modulators, an additional nutrient source and/or a sugar. The plant growth modulators are auxins such as indole-3-acetic acid, α-naphthaleneacetic acid, 2,4-dichlorophenoxyacetic acid and the like, and cytokinins such as kinetin, 6-benzyladenine and the like. The auxin and cytokinin are used alone or in combination at a concentration of up to 5 mM. The nutrient source is casein hydrolyzate or coconut milk. The sugar is, for example, glucose, sucrose or galactose, which is added at a concentration of up to 5% by weight. Alternatively, sugar is not added. The culturing is carried out at about 10° C. to 30° C. for 2 to 18 weeks, in light or dark conditions.

According to the present invention, as described above, an adventitious organ can be generated, by culturing an adventive embryo in a liquid medium or on a solid medium under conditions suitable for the generation of the adventitious organ. Alternatively, the proliferation of an adventive embryo and generation of an adventitious organ can be carried out simultaneously.

Growing adventitious Organ and Production of Podophyllotoxin Compounds

The adventitious organ thus generated can be grown in a conventional liquid medium or on a conventional solid medium under a conventional condition, for example, under the above-mentioned condition, for example, for more than two weeks. During the growing, the adventitious organ produces and accumulates podophyllotoxin compounds in an amount more than that existing in the parent plant.

The podophyllotoxin compounds thus produced can be extracted with an organic solvent for example, an alcohol such as methanol or ethanol, or a ketone such as acetone. The extracted podophyllotoxin can be purified according to a conventional procedure.

Generation of Differentiated Organ

In the present invention, the term "differentiated organ" means tissues having a morphology of an adventitious root or adventitious shoot among the tissues derived from de-differentiated cells or tissue by culturing the cells or tissues in a liquid medium.

The de-differentiated cells or tissue can be prepared by culturing a callus or tissue in a liquid medium or on a solid medium, as described above.

A differentiated organ can be generated by culturing the de-differentiated cells or tissue in a liquid medium, and under conditions suitable for the generation of the differentiated organ. A suitable medium is Murashige-Skoog medium, Linsmaier-Skoog medium or White's medium, preferably supplemented with an additional nutrient source, a sugar, and/or plant growth modulators. The nutrient source is, for example, casein hydrolyzate or coconut milk. The sugar is added at a concentration of up to 3% by weight. Alternatively, sugar is not added. The plant growth modulators are auxin and cytokinin at a ratio of 100:1 to 1:100, and a concentration of each modulator is preferably up to 1 mM. The culturing is carried out at 15° C. to 30° C., for 2 to 10 weeks, in light or dark conditions.

In an embodiment according to the present invention, as described above, a callus or tissue of the Podophyllum plant is prepared; the callus or tissue is cultured in a liquid medium or on a solid medium to obtain a large amount of de-differentiated cells or tissue; the de-differentiated cells or tissue are proliferated by culturing same in a liquid medium; and then the proliferated de-differentiated cells or tissue are cultured in a liquid medium suitable for differentiation, to generate a differentiated organ. Alternatively, in another embodiment, the generation and proliferation of de-differentiated cells or tissue, and the generation of a differentiated organ, can be carried out in one step by culturing a callus or tissue in a liquid medium.

Growing Differentiated Organ and Production of Podophyllotoxin Compounds

The differentiated organ thus generated can be grown on a conventional medium such as agar medium, paper wick medium or filter paper medium, for example, for more than 2 weeks. During the growing, the differentiated organ produces and accumulates podophyllotoxin compounds in an amount more than that existing in the parent plant.

The podophyllotoxin compounds thus produced can be extracted with an organic solvent, for example, an alcohol such as methanol or ethanol, or a ketone such as acetone. The extracted podophyllotoxin can be purified according to a conventional procedure.

According to the present invention, an adventive embryo can be easily and reproducibly obtained, and the adventive embryo can be proliferated to a large amount, or can be used to generate an adventitious organ, which is useful for the production of podophyllotoxin compounds. Moreover, a differentiated organ can be generated from de-differentiated cells or tissue, and the differentiated organ is also useful for the production of podophyllotoxin compounds.

EXAMPLES

The present invention will be further illustrated by, but is by no means limited to, the following examples.

EXAMPLE 1

Formation of Callus

Rhizome of *Podophyllum peltatum* was thoroughly washed with water, sterilized with 70% ethanol for two minutes, sterilized with a 1% sodium hypochlorite aqueous solution for one minute, and rinsed with sterile water. The sterilized rhizome was cut into sections having a length of about 5 mm, in a sterile atmosphere, and the sections were put on a Murashige-Skoog medium containing 3% sucrose, 1% agar, 1 mg/l α-naphthaleneacetic acid, 0.2 mg/l kinetin and 500 mg/l casein hydrolyzate, and cultured by a stationary culture for 5 weeks in the dark, to generate a callus. The callus was passaged several times.

Subjection to Low Sugar Concentration

Next, the thus-prepared callus was put into 100 ml of a liquid Murashige-Skoog medium in a 300 ml flask containing 0.5% by weight sucrose and 500 mg/l casein hydrolyzate, and cultured for 5 weeks at 25° C. in the dark, on a rotary shaker at 130 rpm.

Generation of Adventive Embryo

Thereafter, the above-mentioned culture was transferred to a liquid Murashige-Skoog medium in a 300 ml flask containing 3% by weight sucrose, 1 mg/l α-naphthaleneacetic acid, 0.02 g/l kinetin, and 500 mg/l casein hydrolyzate, and cultured for 2 weeks at 25° C. in the dark, on a rotary shaker at 130 rpm. In the resulting culture, 30% by weight of the cells were an adventive embryo.

COMPARATIVE EXAMPLE 1

Example 1 was repeated except that, in place of the step of subjection to a low sugar concentration, the callus was cultured in the same medium but containing 3% by weight sucrose. In this case, the callus continued to grow, and although a large amount of callus was obtained, an adventive embryo was not obtained.

COMPARATIVE EXAMPLE 2

Example 1 was repeated except, that in the step of the generation of an adventive embryo, the same medium but not containing sucrose was used. In this case, the callus died, and an adventive embryo was not generated.

EXAMPLE 2

Rhizome of *Podophyllum peltatum* was thoroughly washed with water, sterilized with 70% ethanol for two minutes, sterilized with a 1% sodium hypochloride aqueous solution for one minute, and rinsed with sterile water. The sterilized rhizome was cut into sections having a length of about 5 mm, in a sterile atmosphere, and the sections were put on a Murashige-Skoog medium containing 3% sucrose, 1% agar, 1 mg/l α-naphthaleneacetic acid, 0.2 mg/l kinetin and 500 mg/l casein hydrolyzate, and cultured by a stationary culture for 5 weeks in the dark, to generate a callus. The callus was passaged several times.

Next, the thus-prepared callus was put into 100 ml of a liquid Murashige-Skoog medium in a 300 ml flask containing 0.5% by weight sucrose and 500 mg/l casein hydrolyzate, and cultured for 5 weeks at 25° C. in the dark, on a rotary shaker at 130 rpm.

Thereafter, the above-mentioned culture was transferred to a liquid Murashige-Skoog medium in a 300 ml flask containing 3% by weight sucrose, 1 mg/l α-naphthaleneacetic acid, 0.02 g/l kinetin and 500 mg/l casein hydrolyzate, and cultured for 2 weeks at 25° C. in the dark, on rotary shaker at 130 rpm. In the resulting culture, 30% by weight of the cells were an adventive embryo.

The embryo thus-obtained adventive was put on a paper wick medium on a liquid Murashige-Skoog medium containing 3% by weight sucrose, 1 mg/l α-naphthaleneacetic acid, 0.2 mg/l kinetin and 500 mg/l casein hydrolyzate, and cultured by a stationary culture for 4 weeks in the dark to generate an adventitious organ. The adventitious organ was passaged to the same medium and cultured for 4 weeks, and during the culturing, the adventitious organ grew to a length of 2 cm.

The adventitious organ was extracted with ethanol, the extract was assayed by a high performance liquid chromatography (HPLC), and it was found that 1.5% by weight per dry matter of podophyllotoxin was accumulated.

EXAMPLE 3

The adventive embryo of *Podophyllum peltatum* prepared as described in Example 2 was inoculated to 20 ml of a liquid Murashige-Skoog medium containing 3% sucrose, 1 mg/l α-naphthaleneacetic acid, 0.2 mg/l kinetin and 500 mg/l casein hydrolyzate in a 100 ml Erlenmeyer flask, and cultured at 25° C. in the dark on a rotary shaker at 30 rpm for 4 weeks, to generate an adventitious embryo. After culturing in the same medium for 4 weeks in the light, the adventitious organ grew to a length of 1.5 cm.

The adventitious organ was extracted with ethanol, the extract was assayed by HPLC, and it was found that podophyllotoxin in an amount of 0.8% by weight per dry was accumulated.

EXAMPLE 4

Rhizome of *Podophyllum peltatum* was thoroughly washed with water, sterilized with 70% ethanol for two minutes, sterilized with a 1% sodium hypochloride aqueous solution for one minute, and rinsed with sterile water. The sterilized rhizome was cut into sections having a length of about 5 mm, in a sterile atmosphere, and the sections were put on a Murashige-Skoog medium containing 3% sucrose, 1% agar, 1 mg/l α-naphthaleneacetic acid, 0.2 mg/l kinetin and 500 mg/l casein hydrolyzate, and cultured by stationary culture for 5 weeks in the dark, to generate a callus. The callus was passaged several times.

Thereafter, the above-mentioned culture was transferred to a liquid Murashige-Skoog medium in a 300 ml flask containing 3% by weight sucrose, 1 mg/l α-naphthaleneacetic acid, 0.2 mg/l kinetin and 500 mg/l casein hydrolyzate, and cultured for 10 weeks at 25° C. in the dark, on rotary shaker at 130 rpm, to generate a differentiated organ. The differentiated organ was cultured on a solid Murashige-Skoog medium containing 1% agar and 500 mg/l casein hydrolyzate, but not including plant growth modulators, to grow the differentiated organ. The resulting differentiated organ was extracted with ethanol, the extract was assayed by HPLC, and it was found that podophyllotoxin was accumulated in an amount of 1.6% by weight per dry matter.

We claim:

1. A process for preparing an adventive embryo of a plant selected from the group consisting of *Podophyllum peltatum* and *Podophyllum emodi*, comprising the steps of:
    preparing cells of said plant in the form of a callus or cells in a liquid culture;
    incubating the cells in a sugar free medium or a medium containing up to 2%, inclusive, by weight sugar; and then
    incubating the cells in a medium containing more than 2% by weight sugar, to generate an adventive embryo.

* * * * *